(12) United States Patent
Baynham

(10) Patent No.: US 9,956,090 B2
(45) Date of Patent: May 1, 2018

(54) HINGED EXPANDABLE CORPECTOMY DEVICE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 444 days.

(21) Appl. No.: 14/656,312

(22) Filed: Mar. 12, 2015

(65) Prior Publication Data
US 2015/0282939 A1 Oct. 8, 2015

Related U.S. Application Data

(60) Provisional application No. 61/952,068, filed on Mar. 12, 2014.

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/447* (2013.01); *A61F 2002/3024* (2013.01); *A61F 2002/30263* (2013.01); *A61F 2002/30372* (2013.01); *A61F 2002/30373* (2013.01); *A61F 2002/30383* (2013.01); *A61F 2002/30434* (2013.01); *A61F 2002/30556* (2013.01); *A61F 2002/30579* (2013.01); *A61F 2002/30601* (2013.01); *A61F 2002/30629* (2013.01); *A61F 2002/30828* (2013.01); *A61F 2002/4475* (2013.01); *A61F 2230/0084* (2013.01)

(58) Field of Classification Search
CPC ... A61F 2/447; A61F 2002/443; A61F 2/4425
See application file for complete search history.

(56) References Cited

U.S. PATENT DOCUMENTS

| | | | |
|---|---|---|---|
| 2004/0049271 A1* | 3/2004 | Biedermann | A61F 2/44 623/17.11 |
| 2009/0024217 A1* | 1/2009 | Levy | A61B 17/8858 623/17.16 |
| 2013/0023994 A1* | 1/2013 | Glerum | A61F 2/447 623/17.16 |
| 2013/0197642 A1* | 8/2013 | Ernst | A61F 2/442 623/17.16 |
| 2014/0277488 A1* | 9/2014 | Davenport | A61F 2/442 623/17.16 |
| 2014/0277492 A1* | 9/2014 | Wei | A61F 2/442 623/17.16 |
| 2017/0202675 A1* | 7/2017 | Radcliffe | A61F 2/447 |

* cited by examiner

*Primary Examiner* — Zade Coley
*Assistant Examiner* — Olivia C Chang
(74) *Attorney, Agent, or Firm* — McHale & Slavin, P.A.

(57) ABSTRACT

The present invention is directed to an adjustable corpectomy device which fits within the intervertebral distracted channel. The device includes a means for engaging an extendable member to accommodate the distracted channel. The corpectomy implant device is defined by a main body, a first expandable plate, and an opposing second expandable plate. Each expandable plate is adapted to fit within the main body in a compressed state, and extends away from the main body in a non-compressed, expanded state.

7 Claims, 11 Drawing Sheets

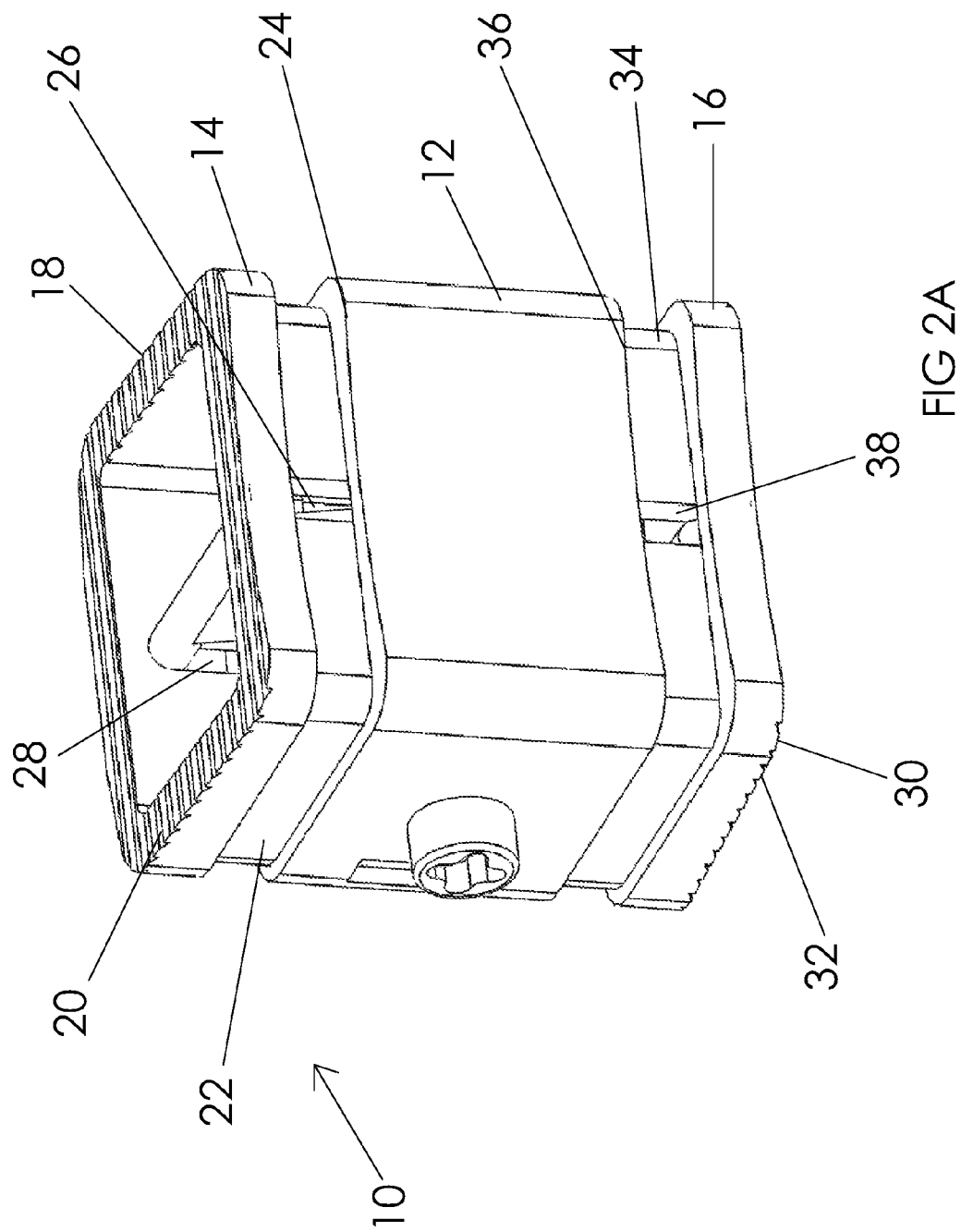

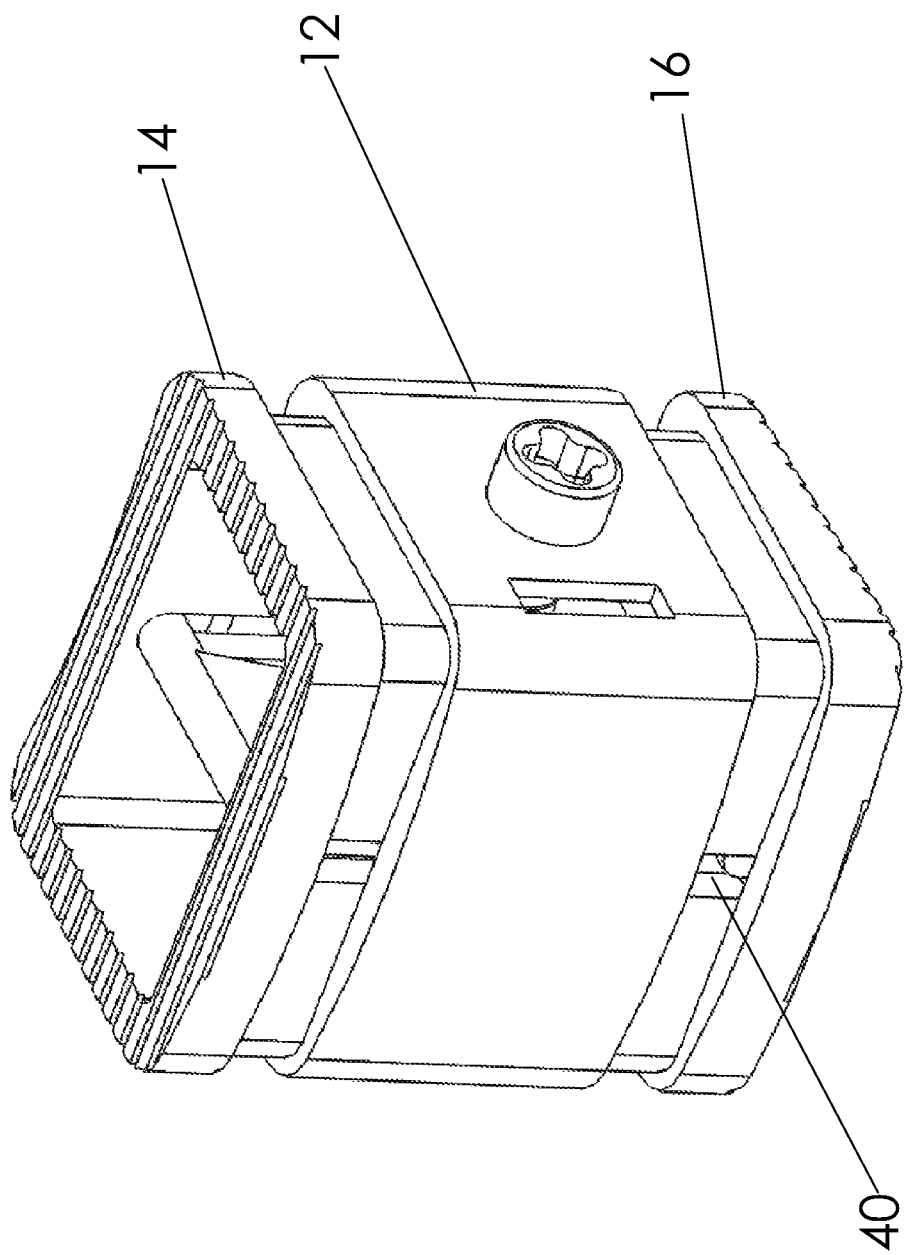

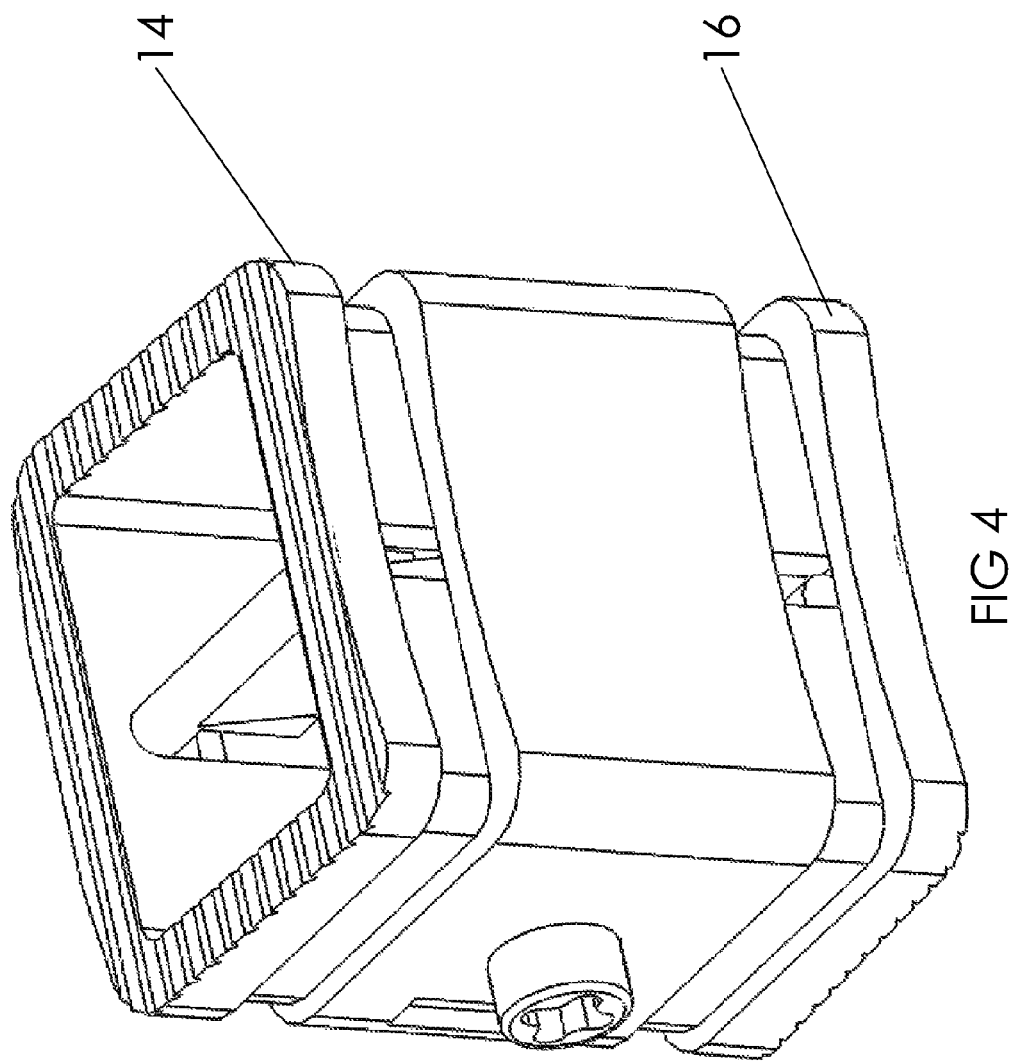

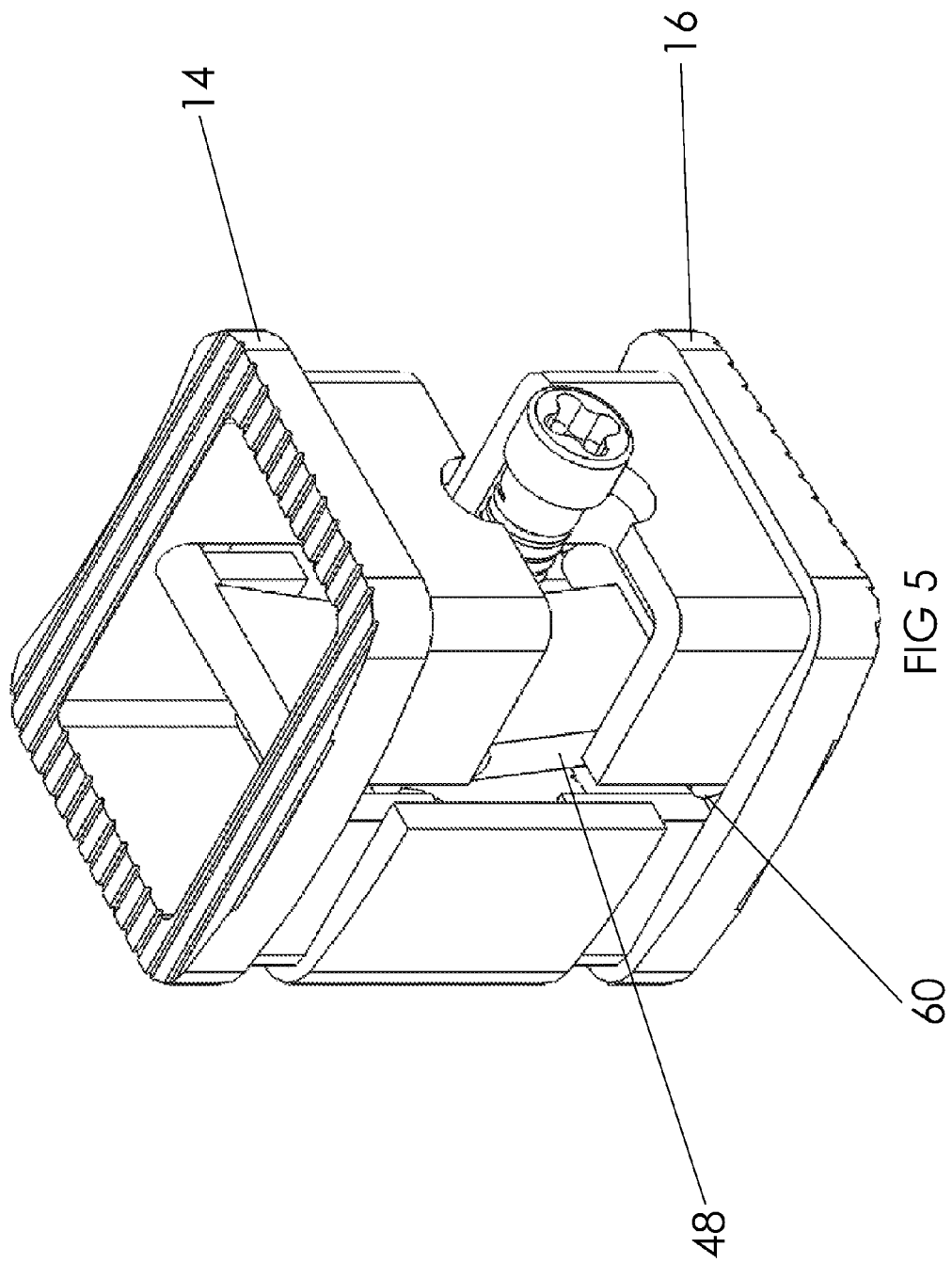

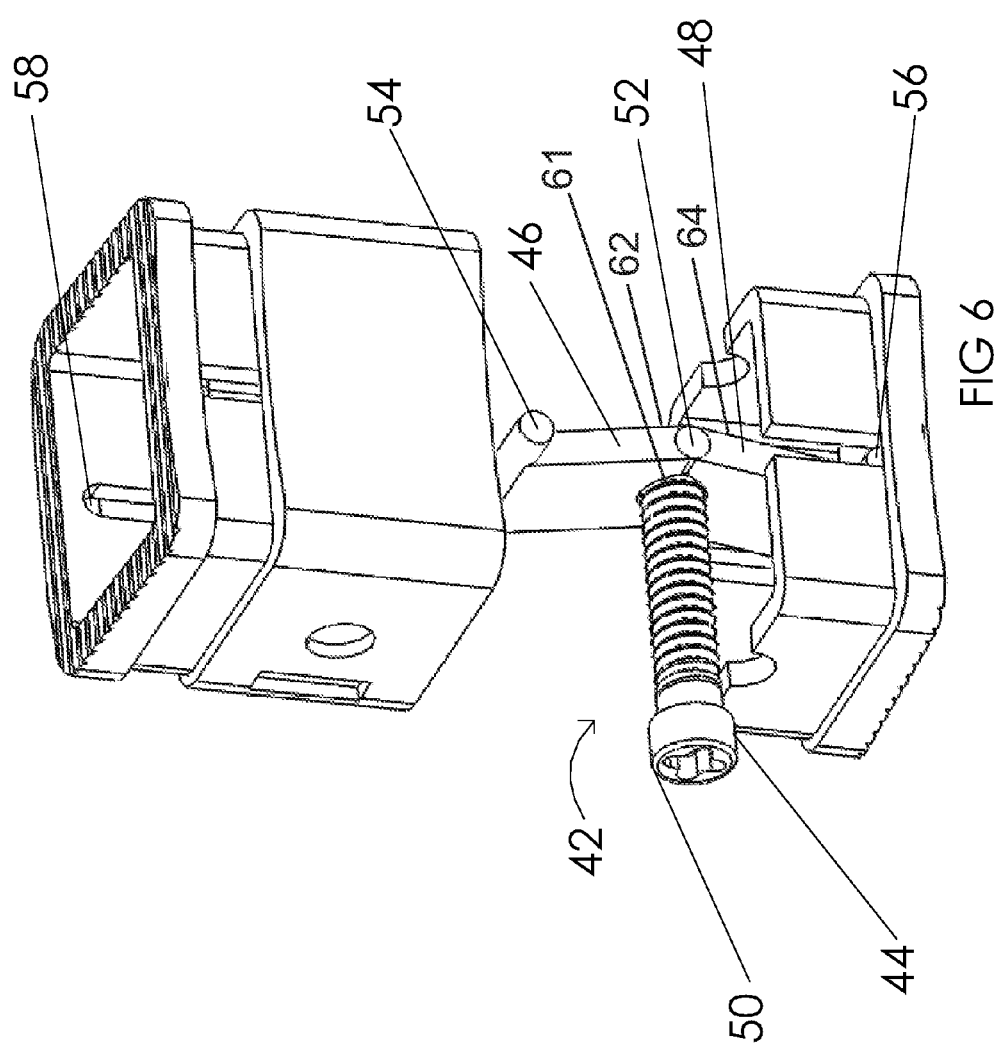

HINGED EXPANDABLE CORPECTOMY DEVICE

PRIORITY CLAIM

In accordance with 37 C.F.R. 1.76, a claim of priority is included in an Application Data Sheet filed concurrently herewith. Accordingly, the present invention claims priority to U.S. Provisional Patent Application No. 61/952,068, entitled "HINGED EXPANDABLE CORPECTOMY DEVICE", filed Mar. 12, 2014. The contents of the above referenced application is incorporated herein by reference in its entirety.

FIELD OF THE INVENTION

The invention generally relates to improvements to vertebral implants and, more particularly, to a longitudinally expandable vertebral implant including telescoping sections configured for incremental expansion by a ratchet expander for ease of securement at any desired increment in situ.

BACKGROUND OF THE INVENTION

The spine consists of vertebrae that are categorized into sections known as the cervical, thoracic and lumbar section in a flexible arranged column. The vertebrae are separated by small cartilaginous cushions known as intervertebral discs. Intervertebral discs are oblate spherical structures that maintain the space between adjacent vertebrae. Each intervertebral disc consists of an outer annulus fibrosus, which surrounds the inner nucleus pulposus. The annulus fibrosus consists of several layers of strong annular fibrocartilage to contain the nucleus pulposus and distribute pressure evenly across the disc wherein a mucoprotein gel serves to absorb shocks.

Deterioration of an intervertebral disc results in limited mobility and can cause severe pain. For instance, normal aging causes the nucleus pulposus to lose fluid and contract in volume resulting in a reduction in the intervertebral space. Any reduction of space between adjacent vertebrae may put pressure on the nerves of the spinal column. Further, a reduction in volume of the nucleus pulposus reduces the disc's ability to absorb shock which can result in disc herniation. The bulge of a herniated disc may also put pressure on nearby nerve structures resulting in pain as well as diminished range of motion.

Surgical options are available including laminectomy and discectomy combined with vertebral fusion and/or dynamic stabilization. However, these surgical options are highly invasive and require prolonged hospitalization and recovery. More recently, artificial disc replacement prosthetics have been used to replace or augment all or part of the removed or resected intervertebral disc.

In order to reduce the pain associated with the movement of the intervertebral joint, surgical intervention is often indicated as a means to alleviate pressure upon the spinal cord while concomitantly stabilizing the associated vertebrae. This involves a surgical procedure to distract the disc and or vertebra, or portions thereof, and the insertion of bone fusing material into the cavity of the opposing vertebra. Corpectomy devices have been developed to help support the spine and maintain the normal spacing between opposing vertebrae. Some of these devices may be packed with fusing material to ensure solid bone growth between the two vertebrae. Typically, corpectomy devices are manufactured at various heights requiring that a cavity between opposing vertebrae to be distracted to a dimension corresponding to the sized corpectomy device. The surgical procedure to prepare the implant site can be difficult and lengthy. Moreover, the procedure can increase risk of trauma to the tissues surrounding of the implant site.

SUMMARY OF THE INVENTION

The present invention is a longitudinally adjustable corpectomy device which fits within the intervertebral distracted channel. The device includes a means for engaging an extendable member to accommodate the distracted channel. An expanding member moves in relation to a main body in accordance with a hinged operation.

An objective of the instant invention to provide a corpectomy device that may be adjusted within the intervertebral cavity or adjusted in situ within the cavity.

It is a further objective of the instant invention to provide an expandable corpectomy which can be expanded by use of a hinged mechanism.

Yet another objective of the instant invention is to provide vertebra engagable endplates which are arranged to pivot and self adjust.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2A a left side perspective view of the corpectomy device in an expanded position;

FIG. 3 is a right side perspective view of the corpectomy device in a expanded position;

FIG. 4 a left side perspective view of the corpectomy device in an expanded position with the main body removed;

FIG. 5 a right side perspective view of the corpectomy device in an expanded position with the main body removed;

FIG. 6 is the perspective view illustrating the expansion member;

DETAILED DESCRIPTION OF THE INVENTION

Figure 1:
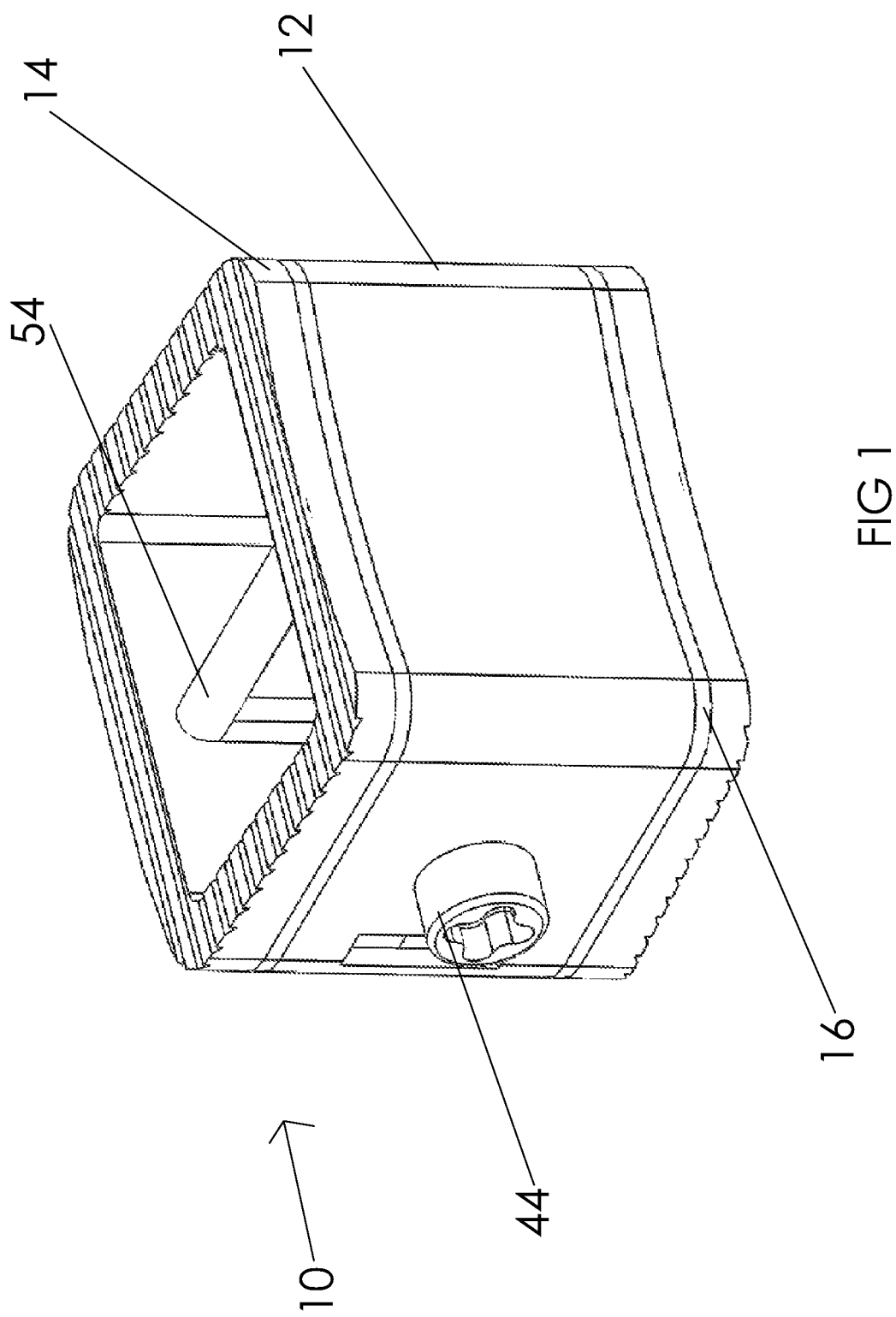
FIG. 1 is a perspective view of the corpectomy device in a compressed position with each plate compressed to the main body.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 2B:
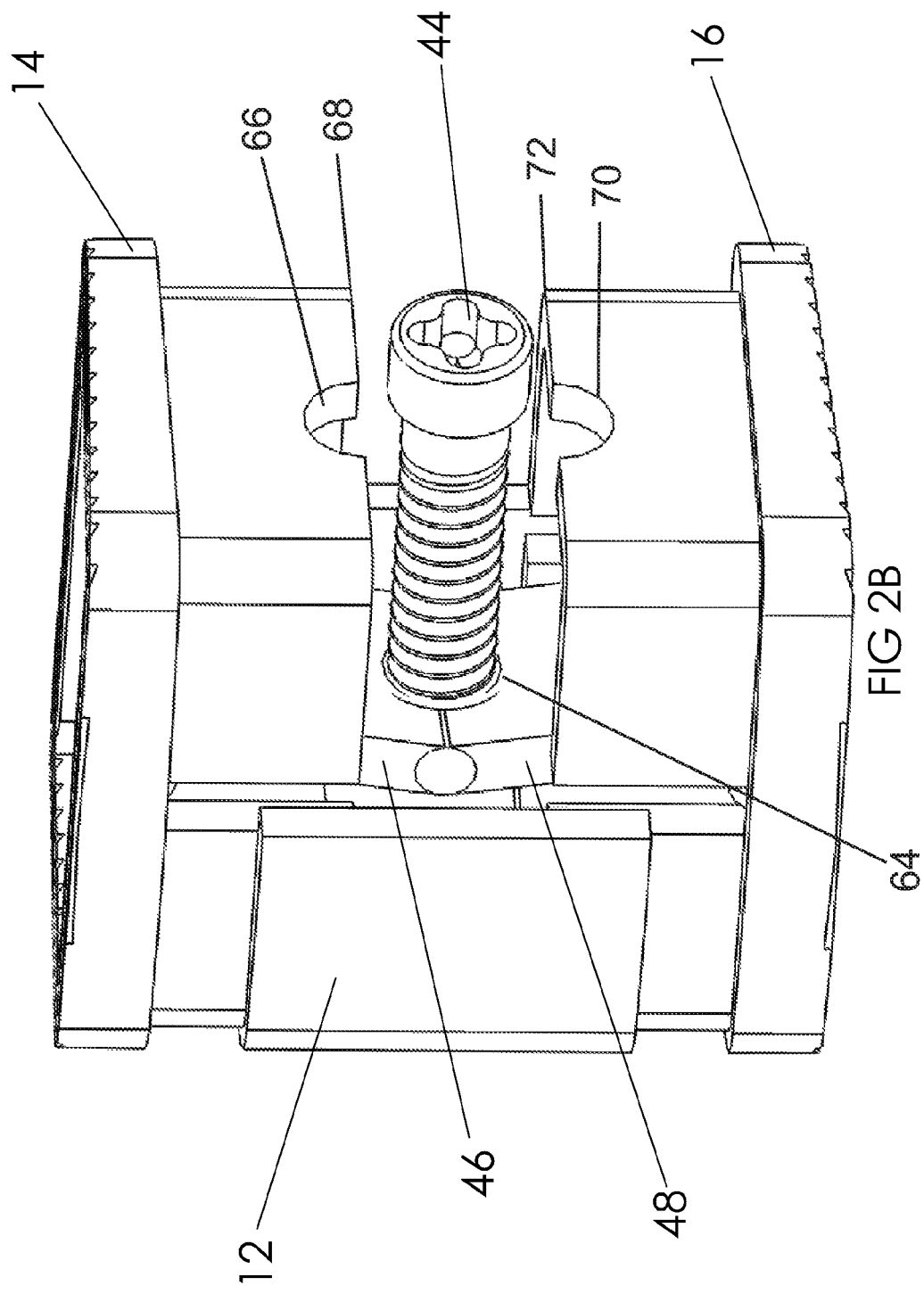
FIG. 2B is left side perspective view of the corpectomy device in an almost fully expanded position.
Figure 7:
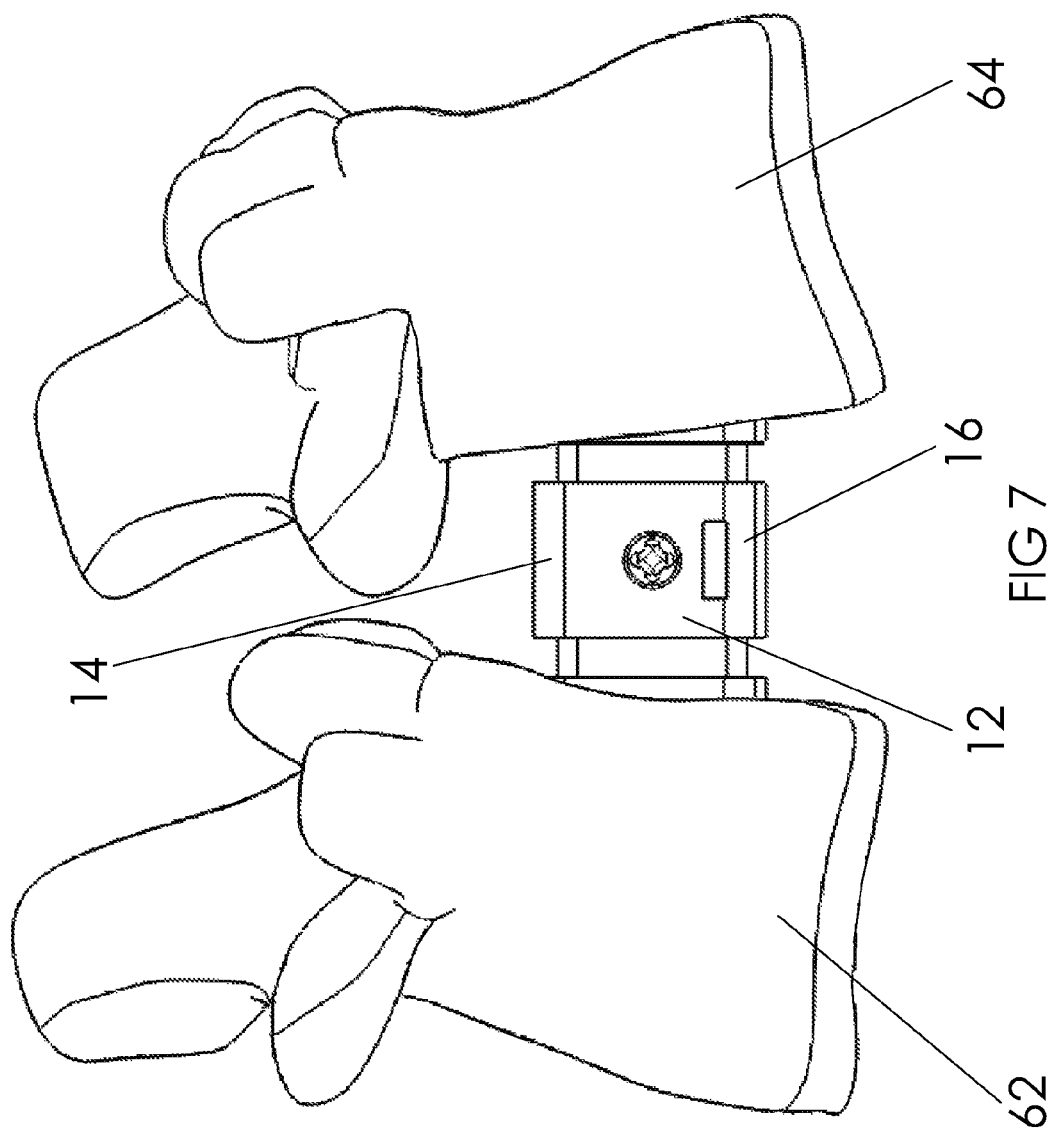
FIG. 7 is a pictorial view depicting the corpectomy device between vertebra in a compressed position.

Referring now to the Figures, set forth is a hinged, expandable corpectomy implant device, referred to generally as 10. The corpectomy implant device 10 is defined by a main body 12, a first expandable plate 14, and an opposing second expandable plate 16. Each expandable plate 14 and 16 is adapted to fit within the main body 12 in a non-expanded state, see FIG. 1. Referring to FIGS. 2A and 2B, in an expanded state, each expandable plate 14 and 16 moves a distance from the main body 12. The expandable plate 14 contains an upper surface 18 which can be smooth. In a preferred embodiment, the upper surface 18 contains surface configurations, such as ridges or teeth 20. The teeth 20 are sized, shaped, and orientated to grip and secure to a surface, such as a vertebral bone. A side wall 22 extends away form the upper surface 18 and is set back to allow for at least a portion of the upper surface 18 to overhang. The first expandable plate upper side wall 22 is inserted into the main body 12 so that in the non-expanded position, the upper surface lies flush with the top end 24 of the main body 12. Two slotted regions 26 and 28 are sized to receive an expansion member to be described later.

The second expandable plate 16 contains an upper surface 30 which can be smooth. In a preferred embodiment, the upper surface 30 contains surface configurations, such as ridges or teeth 32. The teeth 32 are sized, shaped, and orientated to grip and secure to a surface, such as a vertebral bone. A side wall 34 extends away form the upper surface 30 and is set back to allow for at least a portion of the second expandable plate upper surface to overhang. The second expandable plate upper wall side wall 34 is inserted into the main body 12 so that in the non-expanded position, a portion of the second expandable plate 16 lies flush with the bottom end 36 of the main body 12. Two slotted regions 38 and 40 are sized to receive an expansion member to be described later.

To provide for the expandable plates 14 and 16 to traverse between an expanded position and non-expanded position, the corpectomy implant device 10 comprises an expansion member 42, illustrated as a toggle. The expansion member 42 is defined by a screw 44 inserted in a threaded aperture 60 formed along a pivot hinge 52 which adjoins a proximal end 62 of an upper expansion member plate 46 to a proximal end 64 of a lower expansion member plate 48. The screw head 50 is shaped to receive a rotation generating device, such as a drill bit or other driving tool, such as a screw driver, to provide the necessary rotational force to move the expansion member plates 46 and 48 relative to each other. The first plate 14 includes a notch 66 formed in a bottom edge wall 68 and the second plate 16 includes a notch 70 formed in a top edge wall 72. The notches 66 and 70 are constructed to allow passage of the screw shank 45 when the implant is in a compression position.

In use, as the screw 44 is rotated, the expansion member plate 46 and the expansion member plate 48 pivot about hinge 52 from a first position in which the expansion member plates 46 and 48 from a generally V shaped orientation to an expandable state in which the expansion member plates 46 and 48 form a linear structure. Depending on the degree of expansion required, the expansion member plates 46 and 48 may assume a position in-between the non-expanded state and the fully expanded state. The expansion member 42 is designed so that the degree of expansion when the expansion member plates 46 and 48 are in the non-expansion state is greatest. As such, during the first few rotations, the degree of member plate separation is greatest.

As the expansion member plates 46 and 48 reach their most distal heights, i.e. formation of a liner structure, plate separation is more difficult. Such feature allows the surgeon the capability to make fine adjustments at this point.

Positioned at the distal end of each expansion member plate 46 and 48 are generally cylindrical bars 54 and 56. The cylindrical bar 54 is sized and shaped to slidably engage slotted region 28. The cylindrical bar 56 is sized and shaped to slidably engage slotted region 38. As such, when screw 44 is engaged and rotates causing each expansion member plate 46 and 48 to pivot about hinge 52, bar 54 slides within slotted region 28. As the bar contacts the closed end 58, the first expandable plate 14 moves. Concurrently, as bar 56 slides within slotted region 38 and contacts closed end 60, the second expandable plate 16 moves, causing overall expansion.

Figure 8:
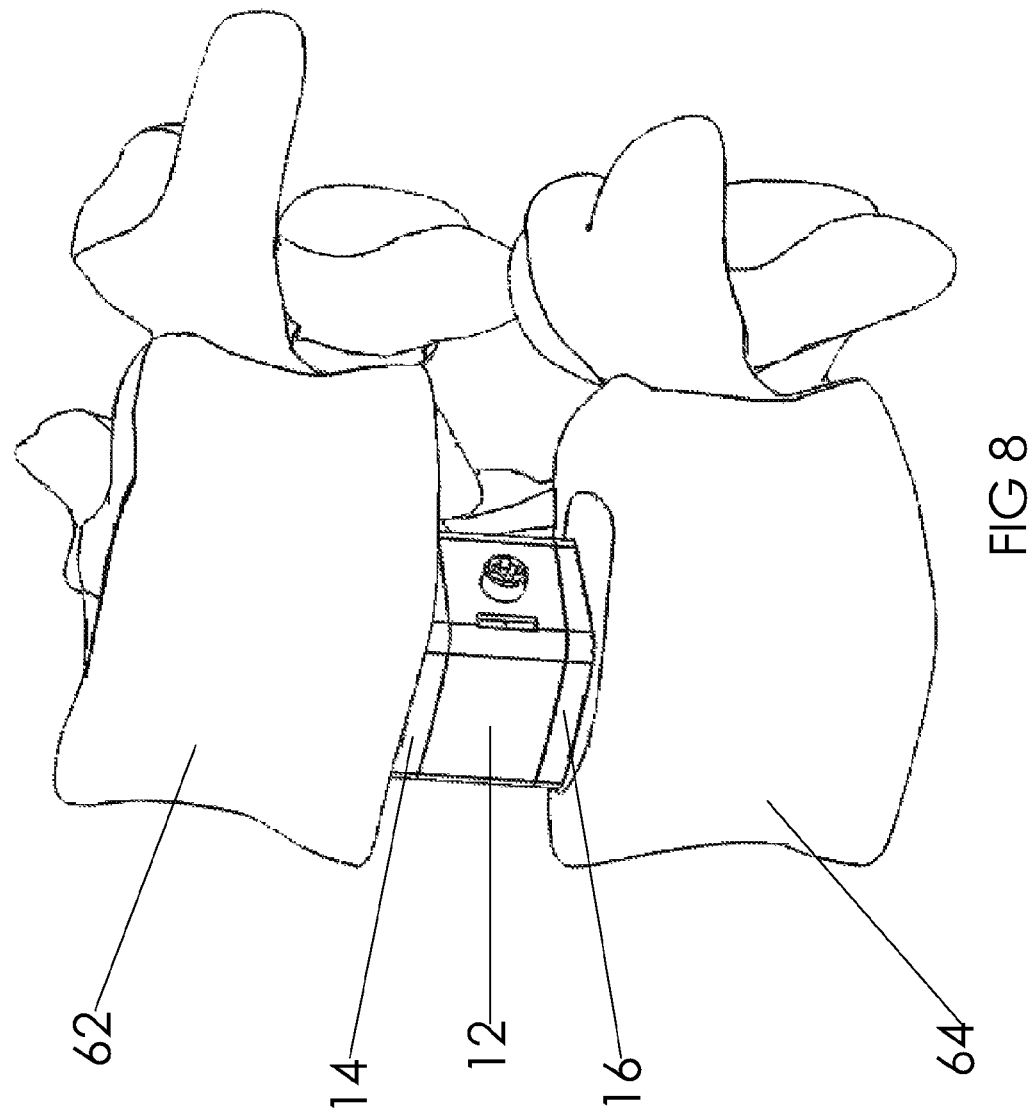
FIG. 8 illustrates the corpectomy implant device in accordance with the present invention in the compressed state between vertebra.
Figure 9:
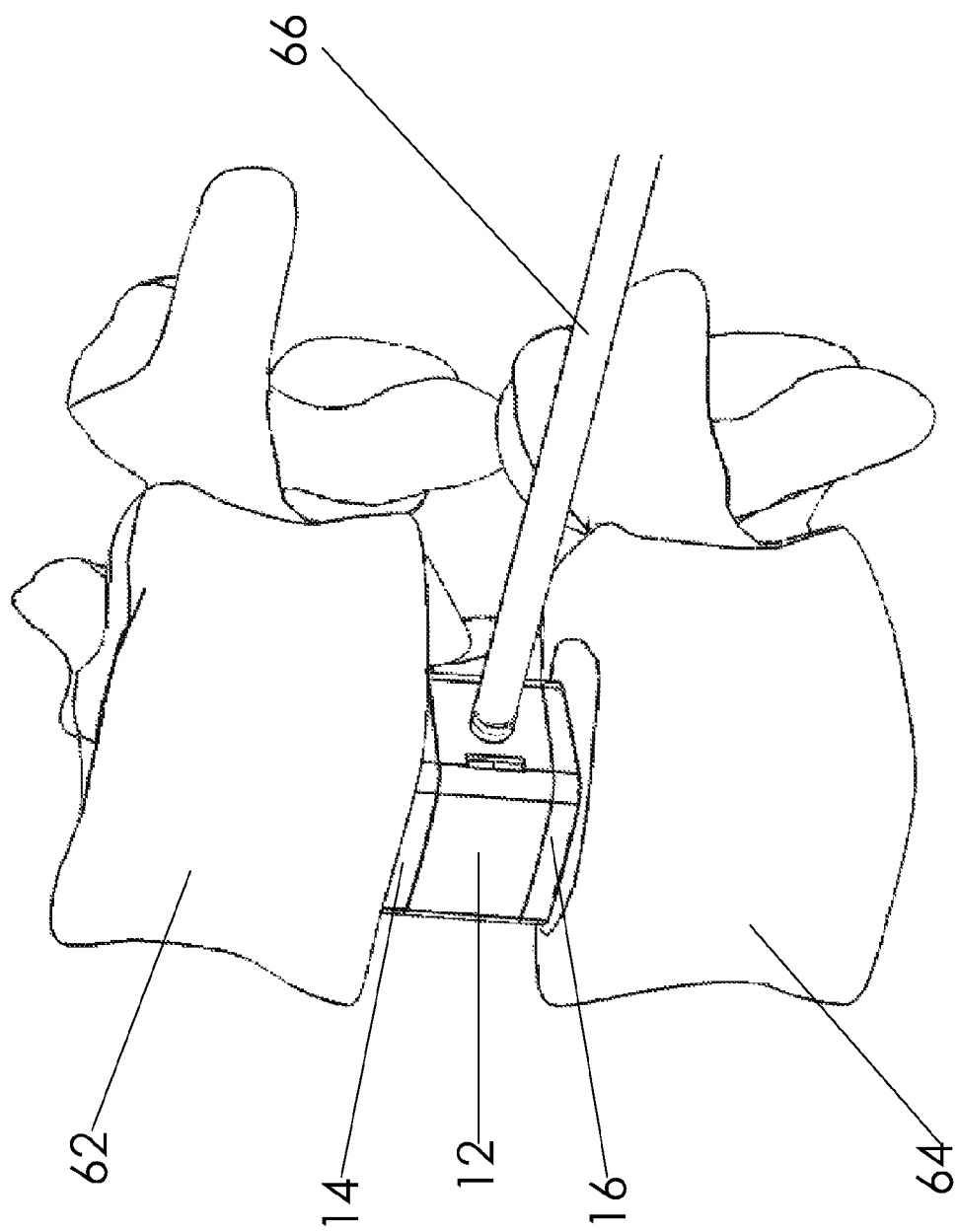
FIG. 9 illustrates the use of a driver.
Figure 10:
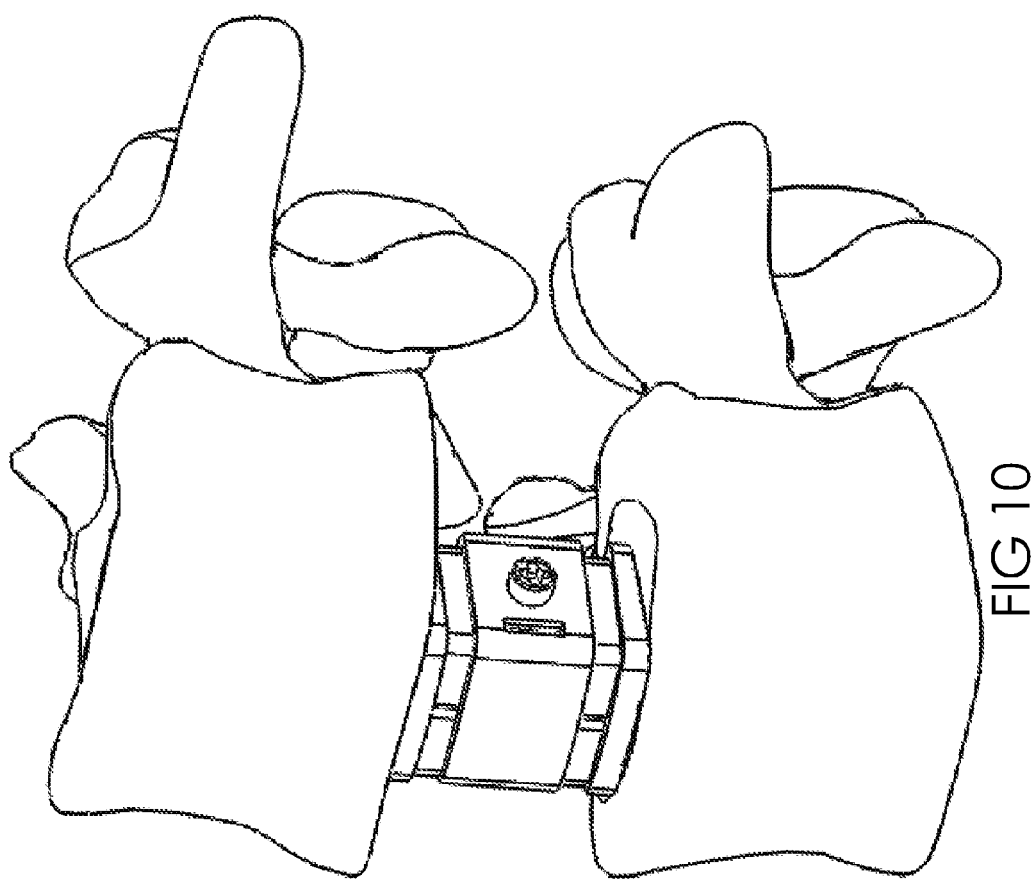
FIG. 10 illustrates the corpectomy implant device in the expanded state.

FIGS. 7-10 are pictorial views depicting the corpectomy implant device 10 between vertebra 62 and 64. FIG. 8 illustrates the corpectomy implant device 10 in the compressed state. FIG. 9 illustrates the use of a driver 66. FIG. 10 illustrates the corpectomy implant device 10 in the expanded state.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An expandable corpectomy implant comprising:
  a housing defined by four walls each having an inner surface forming a substantially square receptacle with an upper edge forming a first end opening and a lower edge end forming a second end opening;
  a first plate having an upper surface with four first plate sidewalls depending therefrom, said first plate sidewalls forming a substantially square frame having an inner surface forming a cavity and an outer surface slidably insertable into said first end opening of said housing receptacle, a pair of centrally disposed slots extending from the upper surface to a bottom edge in opposing first plate sidewalls;

a second plate having a lower surface with four second plate sidewalls depending therefrom, said second plate sidewalls forming a substantially square frame having an inner surface forming a cavity and an outer surface slidably insertable into said second end opening of said housing receptacle, a pair of centrally disposed slots extending from the lower surface to a top edge in opposing second plate sidewalls;

a toggle member for positioning said first plate from said second plate, said toggle member having an upper expansion member plate with a cylindrical bar positioned along a distal end slidably engaging said first plate slots and a proximal end pivotedly coupled to a lower expansion member plate having a cylindrical bar positioned along a distal end slidably engaging said second plate expansion slots;

a screw having a screw head rotatably attached to a wall of said housing having a threaded shank inserted in a threaded aperture formed between said distal ends of said upper and lower expansion member plates;

wherein rotation of said screw will draw said distal ends of said upper and lower expansion member plates toward the screw head whereby said cylindrical bars slide within said first and second plate slots to traverse said first plate and said second plate between an expanded position and a non-expanded position.

2. The expandable corpectomy implant according to claim 1 wherein said first plate includes a notch formed in said bottom edge and said second plate includes a notch formed in said top edge, said notches constructed to allow passage of said screw shank when said implant is in the non-expanded position.

3. The expandable corpectomy implant according to claim 1 wherein said upper surface of said first plate is smooth.

4. The expandable corpectomy implant according to claim 1 wherein said upper surface of said first plate includes surface configurations.

5. The expandable corpectomy implant according to claim 4 wherein said surface configurations are teeth orientated to grip vertebral bone.

6. The expandable corpectomy implant according to claim 1 wherein said sidewalls of said first plate extend away from an edge of said upper surface.

7. The expandable corpectomy implant according to claim 1 wherein said sidewalls of said second plate extend away from an edge of said lower surface.

* * * * *